United States Patent
Monteverde et al.

(10) Patent No.: US 11,672,602 B2
(45) Date of Patent: Jun. 13, 2023

(54) PORT PLACEMENT GUIDE BASED ON INSUFFLATED PATIENT TORSO MODEL AND NORMALIZED SURGICAL TARGETS

(71) Applicant: Verb Surgical Inc., Santa Clara, CA (US)

(72) Inventors: David R. Monteverde, Sunnyvale, CA (US); Danyal Fer, Oakland, CA (US); Andrew Bzostek, San Jose, CA (US)

(73) Assignee: Verb Surgical Inc., Santa Clara, CA (US)

( * ) Notice: Subject to any disclaimer, the term of this patent is extended or adjusted under 35 U.S.C. 154(b) by 285 days.

(21) Appl. No.: 16/894,625

(22) Filed: Jun. 5, 2020

(65) Prior Publication Data

US 2021/0378746 A1 Dec. 9, 2021

(51) Int. Cl.
| | |
|---|---|
| *A61B 34/10* | (2016.01) |
| *G06T 17/00* | (2006.01) |
| *A61B 34/37* | (2016.01) |
| *A61B 90/00* | (2016.01) |
| *A61B 34/30* | (2016.01) |

(52) U.S. Cl.
CPC .............. *A61B 34/10* (2016.02); *A61B 34/37* (2016.02); *A61B 90/06* (2016.02); *A61B 90/36* (2016.02); *G06T 17/00* (2013.01); *A61B 2034/105* (2016.02); *A61B 2034/107* (2016.02); *A61B 2034/302* (2016.02); *A61B 2090/364* (2016.02)

(58) Field of Classification Search
CPC ......... A61B 34/10; A61B 34/37; A61B 90/06; A61B 90/36; A61B 2034/105; A61B 2034/107; A61B 2034/302; A61B 2090/364; A61B 17/3421; A61B 17/3423; A61B 2034/102; G06T 17/00–30

See application file for complete search history.

(56) References Cited

U.S. PATENT DOCUMENTS

| | | | | |
|---|---|---|---|---|
| 9,320,421 | B2 * | 4/2016 | Chabanas | G06T 7/75 |
| 9,547,940 | B1 * | 1/2017 | Sun | G06T 7/344 |
| 9,782,152 | B2 * | 10/2017 | Miga | G06T 7/521 |
| 10,226,302 | B2 * | 3/2019 | Lacal | G16H 20/40 |
| 10,417,357 | B2 * | 9/2019 | Franklin | A61B 90/39 |

(Continued)

OTHER PUBLICATIONS

Vilos et al., "Effect of body habitus and parity on the initial Veres intraperitoneal CO2 insufflation pressure during laparoscopic access in women", 2006 (Year: 2006).*

(Continued)

*Primary Examiner* — Phong X Nguyen
(74) *Attorney, Agent, or Firm* — Aikin & Gallant, LLP

(57) ABSTRACT

A method for determining surgical port placement for minimally invasive surgery. Based on received measurements, an instance of a parametric torso model that defines an external surface and a visceral surface each having a dome shape that takes into account an insufflation effect, is determined. Normalized surgical target locations in the parametric torso model are determined in response to an identification of a surgical procedure, and are mapped to un-normalized surgical target locations. Permissible port locations on the instance of the parametric torso model are computed, based on the characteristics of a surgical tool and based on the un-normalized surgical target locations. Other aspects are also described and claimed.

20 Claims, 11 Drawing Sheets

(56) References Cited

U.S. PATENT DOCUMENTS

| | | | | |
|---|---|---|---|---|
| 10,706,614 | B1* | 7/2020 | Zatonyi | G06T 15/503 |
| 11,213,353 | B2* | 1/2022 | Frushour | G06Q 50/22 |
| 11,284,955 | B2* | 3/2022 | Yu | G02B 27/017 |
| 11,324,561 | B2* | 5/2022 | Fan | A61B 1/008 |
| 2003/0109780 | A1* | 6/2003 | Coste-Maniere | G06T 7/0012 |
| | | | | 600/407 |
| 2012/0253515 | A1* | 10/2012 | Coste-Maniere | A61B 34/10 |
| | | | | 700/250 |
| 2013/0287294 | A1* | 10/2013 | Ye | G06T 17/00 |
| | | | | 382/154 |
| 2014/0133727 | A1* | 5/2014 | Oktay | G06T 7/33 |
| | | | | 382/131 |
| 2014/0148816 | A1* | 5/2014 | McDonald | A61B 34/10 |
| | | | | 606/130 |
| 2016/0022375 | A1* | 1/2016 | Blake | A61B 34/10 |
| | | | | 600/424 |
| 2016/0379419 | A1* | 12/2016 | Khalili | G06T 19/20 |
| | | | | 345/419 |
| 2019/0321115 | A1 | 10/2019 | Anderson et al. | |
| 2020/0113636 | A1 | 4/2020 | Chino et al. | |
| 2020/0202622 | A1* | 6/2020 | Gallo | G06T 17/205 |
| 2020/0345438 | A1* | 11/2020 | Stricko, III | A61B 34/10 |
| 2021/0228282 | A1* | 7/2021 | Dimaio | A61B 34/20 |
| 2021/0378746 | A1* | 12/2021 | Monteverde | A61B 34/37 |
| 2022/0054772 | A1* | 2/2022 | Sterke | A61M 16/024 |
| 2022/0096197 | A1* | 3/2022 | Song | A61B 90/36 |

OTHER PUBLICATIONS

Patient-specific port placement for laparoscopic surgery using atlas-based registration, Enquobahrie et al., 2013 (Year: 2013).*

Optimal Dexterity for a Snake-like Surgical Manipulator using Patient-specific Task-space Constraints in a Computational Design Algorithm, Razjigaev et al., 2019 (Year: 2019).*

Monteverde, David R., "Kinetics for Robotics and Biomechanics", Sep. 2012, 37 pages.

International Search Report and Written Opinion for International Application No. PCT/US2021/033517 dated Aug. 25, 2021, 15 pages.

J. Bano et al., "Simulation of the Abdominal Wall and Its Arteries after Pneumoperitoneum for Guidance of Port Positioning in Laparoscopic Surgery", Advances in Visual Computing, Springer Berlin, Heidelberg, Berlin, Jul. 16, 2012, pp. 1-11.

Mafalda Camara et al., "Subject-specific modelling of pneumoperitoneum: model implementation, validation and human feasibility assessment", International Journal of Computer Assisted Radiology and Surgery, Springer, DE, vol. 14, No. 5, Feb. 20, 2019, pp. 841-850.

O. Weede et al., "Knowledge-based Planning of Port Positions for Minimally Invasive Surgery", 2013 IEEE Conference on Cybernetics and Intelligent Systems (CIS), Nov. 12, 2013, pp. 12-17.

International Preliminary Report on Patentability for International Application No. PCT/US2021/033517 dated Dec. 15, 2022, 9 pages.

* cited by examiner

| Control Ellipse | level [X] | lateral radius [Y] | dorsal radius [Z] | ventral radius [Z] | dorsal offset [Z] |
|---|---|---|---|---|---|
| Hip | 0 | radius_lateral_hip | radius_dorsal_hip | radius_dorsal_hip | 0 |
| Waist | level_waist | radius_lateral_waist | radius_dorsal_waist | radius_ventral_waist | offset_waist |
| Chest | level_chest | radius_lateral_chest | radius_dorsal_chest | radius_dorsal_chest | 0 |
| Upper chest | level_upperchest | =radius_lateral_chest | radius_dorsal_upperchest | radius_dorsal_upperchest | 0 |

FIG. 3

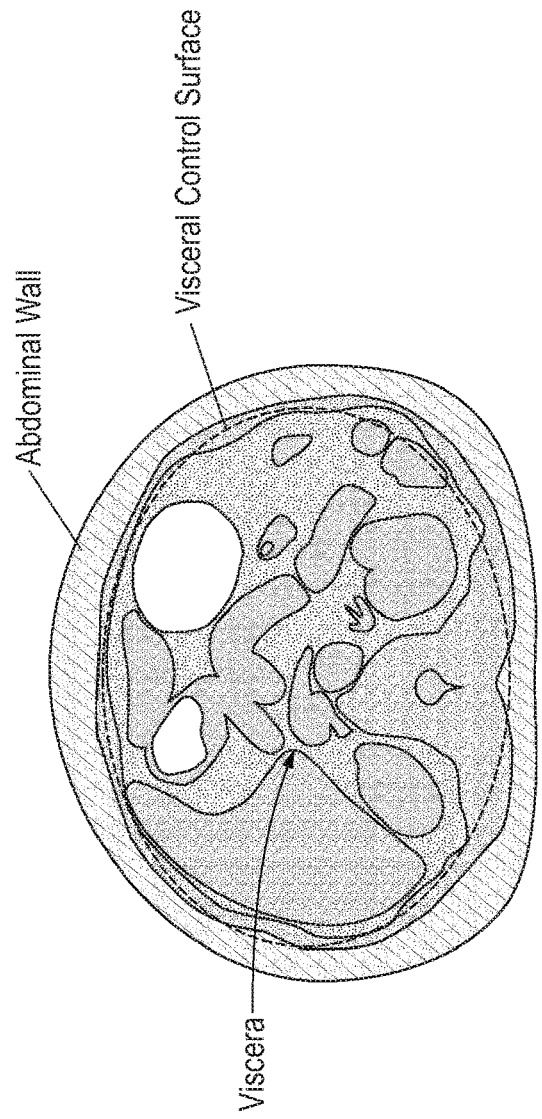

FIG. 4

PORT PLACEMENT GUIDE BASED ON INSUFFLATED PATIENT TORSO MODEL AND NORMALIZED SURGICAL TARGETS

FIELD

Various aspects of the disclosure here relate to the design of surgical tools for minimally invasive surgery, MIS, and robotically assisted MIS.

BACKGROUND

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a blade, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can be performed faster and with less surgeon fatigue using a surgical robotic system in which the surgical tools are operatively attached to the distal ends of robotic arms, and a control system actuates the arm and its attached tool. The tip of the tool will mimic the position and orientation movements of a handheld user input device (UID) as the latter is being manipulated by the surgeon. The surgical robotic system may have multiple surgical arms, one or more of which has an attached endoscope and others have attached surgical instruments for performing certain surgical actions.

Manufacturers of surgical tools designed for MIS may be asked to specify a list of anatomies in a reference patient torso model, that can be reached by a given a surgical tool design. That is a challenging question to answer. A subjective solution to this problem is to develop a virtual reality model of the anatomy (in the reference patient torso model), and then perform a virtual reality simulation that shows whether or not a given surgical tool can reach a given part of the anatomy. With that solution however, the manufacturer of the surgical tool is not able to specify the requirements for use of the tool, or under what circumstances is the surgical tool expected to work (pass) and under what circumstances the tool is not expected to work (fail.)

SUMMARY

The requirements for use of an MIS tool should be specified in the form of a geometric model of the human torso that takes into account the effect of insufflation on the torso. One aspect of the disclosure here is a set of criteria for making a pass/fail determination on whether an anatomy of a reference patient can be reached by a given a surgical tool design, for MIS. The determination in turn provides guidance on placement of a surgical port (where the surgical tool would be inserted on the reference patient) to perform minimally invasive surgeries such as endoscopic surgery (e.g., where the tool is a laparoscopic, hand-held surgical instrument) and robotically assisted endoscopic surgery (e.g., where the tool is a wristed surgical instrument or endoscope that is attached to a surgical robotic arm having a certain number of links and motorized joints.)

A parametric, geometric patient torso model is described that is based on an elliptical cylinder. In one aspect, several reference patient sizes are instantiated for the model, based on two or more of the following parameters: stature, waist circumference, body mass index (BMI), and gender of the reference patient, thereby yielding parametric models for arbitrary size patient. BMI may be computed based on height and weight of the patient.

Surgical target locations in normalized coordinates in the model are determined, for specified activities of a given surgical procedure, and these are then mapped to corresponding (un-normalized) locations in the instantiated, reference patient sizes.

Surgical port locations in normalized coordinates on an access surface of the model are determined, based on the tool reach range of a given surgical tool, and based on the surgical target locations inside the torso model. These are then mapped to corresponding (un-normalized) surgical port locations in each of the instantiated, reference patient sizes. A reachability map may be generated for each of the reference patient sizes, which shows the locations on the access surface of the reference patient size where surgical ports are permitted to be placed (through which the particular surgical tool can reach the relevant surgical target locations.)

Another application of the parametric, geometric patient torso model is a process that, based on a given surgical target location in the torso model as input, provides as its output a set of permissible, surgical port locations and a required reach for a surgical tool (that is to be used in minimally invasive surgeries such as endoscopic or laparoscopic surgery and robotically assisted endoscopic/laparoscopic surgery.)

Another application of the model is a process that outputs an objective assessment of a surgical robotic functionality such as the reach of a surgical tool and the available clearance around the tool or around a target surgical location.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

FIG. 3 is a table that summarizes an example parameterization of the elliptic cylinder.

FIG. 4 illustrates a visceral control surface and abdominal wall that can also be modeled by an elliptic cylinder, as part of the parametric, geometric patient model.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known structures and techniques have not been shown in detail so as not to obscure the understanding of this description.

Torso Model

A parametric, geometric patient torso model is described that is scalable according to a plurality of dimensionalities or parameters, being for example standard anthropometric measurements that are two or more of stature, waist circumference, body mass index (BMI), and gender. Several instances of the model are generated that represent human torsos of different sizes (reference patient sizes), intended to cover a significant portion of the patient population. The model predicts or outputs a visceral surface and an external surface (e.g., as wire frames), and takes in account the effects of insufflation on the torso.

Figure 1:
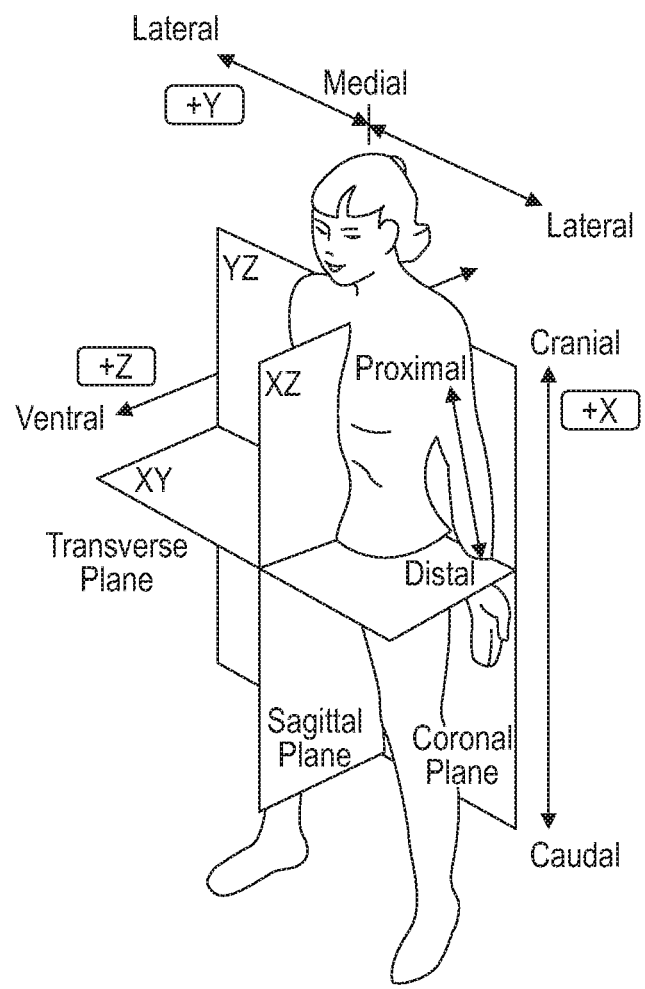
FIG. 1 shows reference anatomical axes and planes (or a reference frame) used in a parametric, geometric patient torso model.
Figure 2:
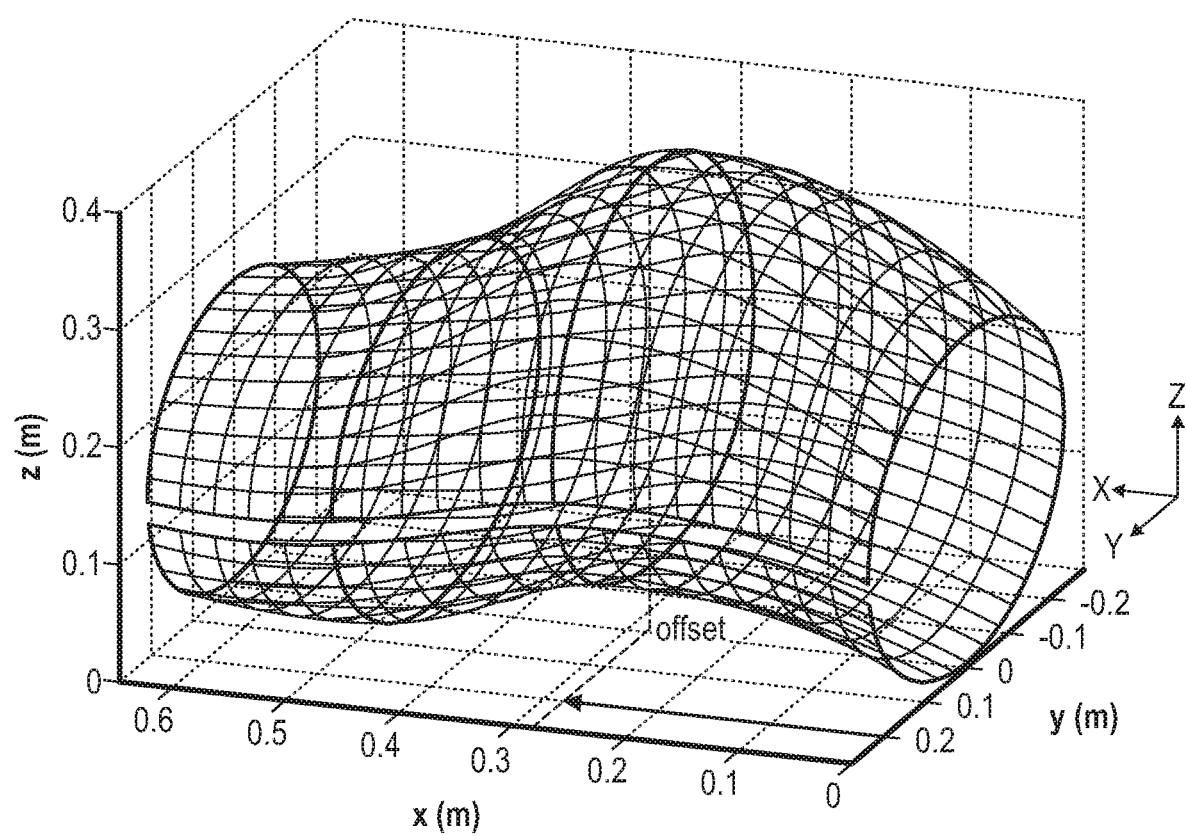
FIG. 2 illustrates a human torso modeled as an elliptic cylinder with features exaggerated.

The model will be illustrated using the reference anatomical axes and planes shown in FIG. 1. In the model, cross sections of the torso are abstracted as ellipses such as seen in the example of FIG. 2 and the shape of the torso is represented by a surface of a generalized elliptic cylinder (or simply, elliptic cylinder) whose cross sections in transverse planes (planes normal to the X axis) are several ellipses. The surface is symmetric with respect to the midsagittal plane (the XZ plane). Each cross section can have an offset with respect to the dorsal plane (the XY plane.)

In one aspect, the elliptic cylinder surface is controlled by or defined by four elliptical cross sections as shown in FIG. 2, namely the cross sections at the hip plane, waist plane, chest plane and upper chest plane. Because of this simplification, the elliptic cylinder can be described by a relatively small number of parameters, such as the five parameters shown in FIG. 3. For finer granularity however, the elliptic cylinder surface may be defined by more than four elliptical cross sections and/or by more than five parameters.

In one aspect of the disclosure here, one or more of the constituent elliptical cross sections is composed of two half ellipses (a ventral or upper half ellipse joined to a dorsal or bottom half ellipse) that may have different radii of curvature. Such a cross section is also referred to as a "duo" of two half ellipses. In one aspect, at least one such cross section duo is through the waist plane which better models the effects of insufflation as compared to a regular ellipse. The cross sections at the ends of the torso, namely the end upper chest plane and the hip plane, may be regular ellipses. In another aspect, all four cross sections are duos. Referring to the table in FIG. 3 as an example, each cross section in this case is a duo. A duo may be characterized by the five parameters shown: a radial dimension along the mediolateral (Y) direction, two radial dimensions along the dorsoventral (Z) direction (one ventral and one dorsal), a position along the caudocranial (X) axis, and a dorsal offset. The dorsal offset may be used to account for spinal curvature (when the torso is in the supine position as shown in the figure.) Note the following in connection with the table of FIG. 3:

Level is defined as caudocranial (X) position with respect to the origin of the model (hip level is zero);

Upper chest breadth (lateral, excluding arms) is assumed the same as that of the chest;

Lateral radii are half of the breadths, and dorsal radii are half of the depths;

Ventral radii for the hip, chest and upper chest are the same as dorsal radii; and Ventral radius at the waist is used to account for insufflation (this will be detailed below), but in non-insufflated state, it is the same as dorsal radius.

The elliptic cylinder can be used to approximate not only the external shape of the torso (also referred to here as the external surface) but also deeper anatomy such as the surface of the visceral cavity (also referred to here as the visceral surface.) In other words, in addition to the external surface the model may also define a visceral surface (also referred to as a visceral control surface) as seen in FIG. 4. The visceral control surface may be inferred, based on the external surface for example as summarized in the table FIG. 3 (in non-insufflated state) and based on an abdominal wall thickness. The latter may be presumed to be uniform throughout the torso (based on studies reporting on subcutaneous fat and muscle thickness), except in the vicinity of breasts and "love handles" which may be a function of a desired, body mass index, BMI. In other words, the abdominal wall thickness may be computed as a function of an input BMI. Such an abstraction of the visceral control surface enables the mapping of corresponding organ locations between models of different sizes and bariatricities (the mapping is described below.)

Insufflation of the Abdomen

One element of laparoscopic surgery is the creation of an abdominal workspace by pumping gas (for example carbon dioxide) into the peritoneal cavity. This creation of abdominal workspace is known as insufflation. As an abdomen becomes insufflated, three phases can be observed: reshaping, stretching and pressurization—see diagrams in FIG. 5. Reshaping occurs over a relatively small increase of intra-abdominal pressure (IAP), which nonetheless changes the waist plane cross-section from a rather wide elliptical shape into a more circular cross-sectional shape. The second phase of insufflation (stretching) involves a higher IAP value and an increase in the abdominal cross-section while maintaining the near-unitary aspect ratio (quasi-circular shape). After some stretching, the stiffness of the abdominal wall transitions to a markedly higher value, such that small increases in abdominal volume require very large increases in pressure.

Abdominal compliance is highly variable amongst the patient population (as shown by the two sample curves in FIG. 5) and is particularly difficult to predict in obese patients. Having said that, it is noted that the insufflation behavior described here includes TAP levels that would not be nominally expected during surgery. During normal laparoscopy (with insufflation pressures limited to around 15 mm Hg), the abdomen either does not enter or barely starts transition into the third phase. Therefore, based on the general behavior observed within the range of interest of TAP, one can assume that typical insufflation during laparoscopic surgery lands in the stretching phase (pressurization phase is typically not entered).

Figure 5:
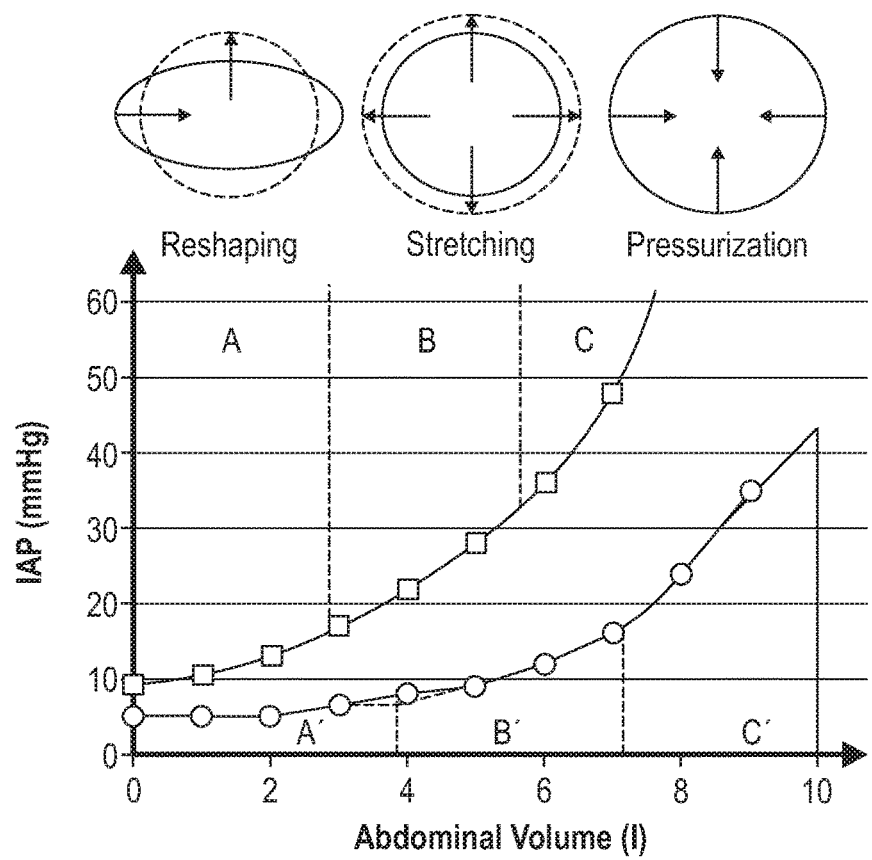
FIG. 5 shows the reshaping and stretching phases of an abdominal cross section during insufflation.

As seen from FIG. 5, during the reshaping phase the lateral dimension of the abdominal cross-section decreases, but subsequently increases during the stretching phase (the change reverses). Meanwhile, the dorsoventral dimension increases during both phases. Accounting for this effect, one aspect of the disclosure here is to configure the model so that it makes an additional assumption that the net change in lateral dimension of the waist plane cross-section is near zero, while the major effect of insufflation goes towards increasing its dorsoventral dimension. That captures the general behavior of abdominal insufflation, while minimizing information content.

Abdominal insufflation does not significantly affect torso cross-sections at the hip or chest levels. This is partly due to osseous constraints. Caudally, the abdomen is constrained by the pelvis, while cranially it is constrained by the rib cage. Dorsally, the entire torso is constrained by the spinal column. This means that the volumetric effects of insufflation are mainly manifested in a change of cross-sectional shape in the ventral waist region, consistent with the behavior of the model described here. The effects outlined here can be observed in the dome-like shape of an inflated abdomen.

More generally, in one aspect of the disclosure here, the effect of insufflation on the torso elliptical cylinder is achieved in the model by increasing the ventral radius of the waist plane ellipse, while other control ellipses (hip, chest and upper chest) are left unchanged, relative to non-insufflated state. More specifically, a distention factor fdistention is determined that can be used to compute supine abdominal height (SAH) when insufflated, based on the SAH when deflated, using the relation:

$$SAHinsufflated = fdistention \cdot SAHdeflated$$

Figure 6:
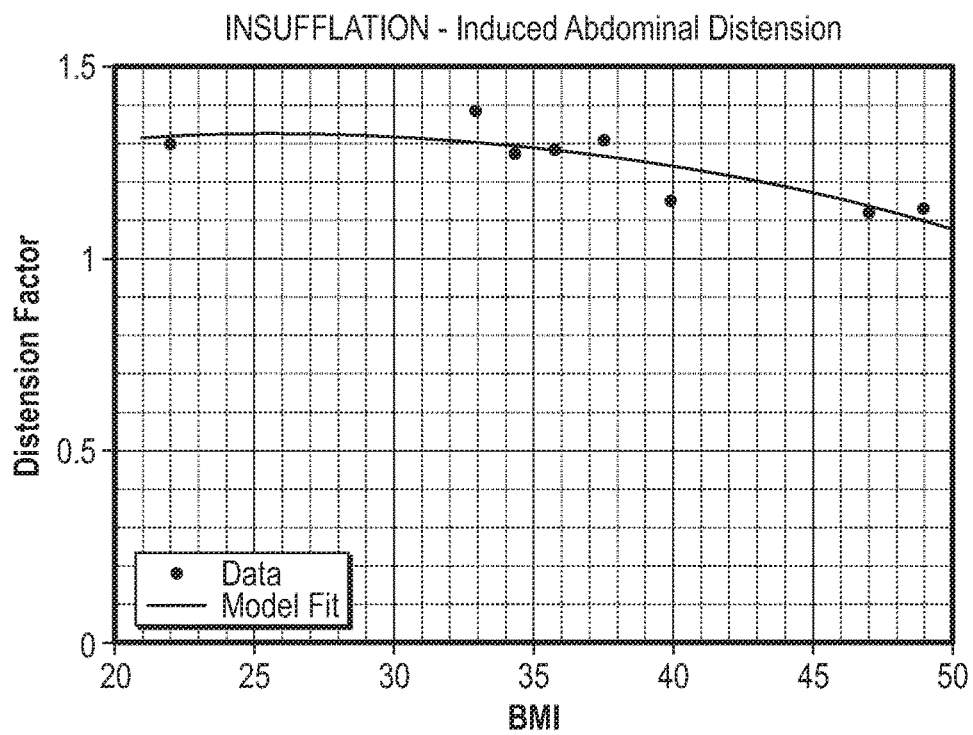
FIG. 6 shows a plot that illustrates insufflation-induced abdominal distension.
Figure 7A:
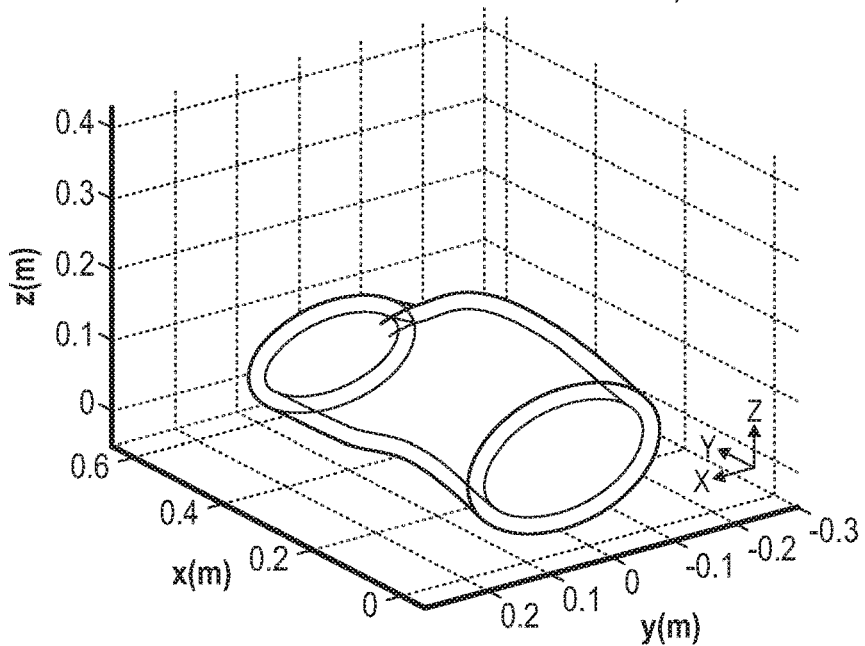
FIGS. 7A-7D are four example, patient reference sizes of the parametric, geometric patient torso model.
Figure 7B:
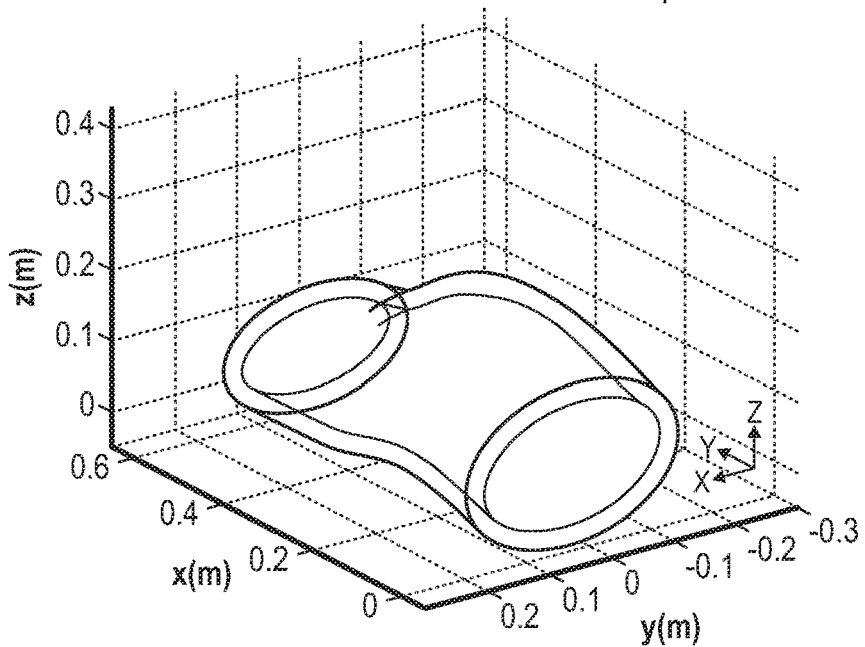
Figure 7C:
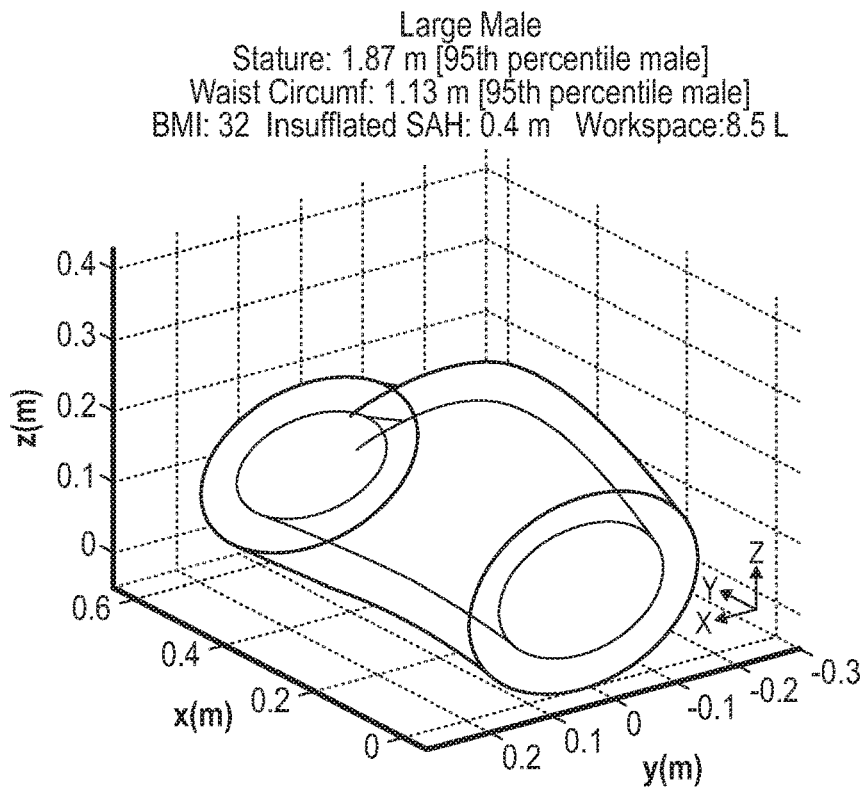
Figure 7D:
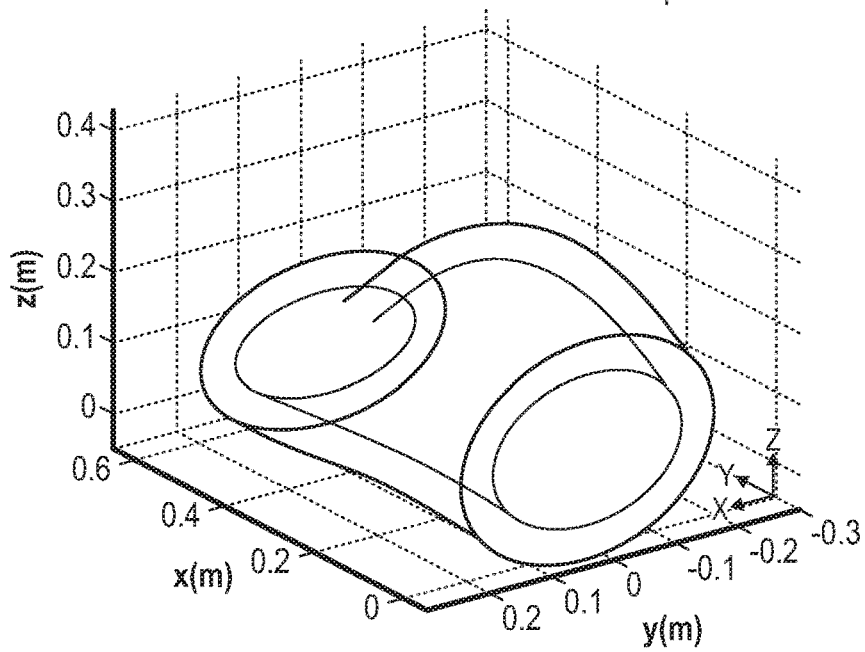

Several distention factors were evaluated and plotted against BMI as shown in FIG. 6 (specifically, points to the right of BMI=32). The trend of this data shows decreasing distention factor for increasing BMI in obese patients. A potential reason for this is that a relatively consistent insufflation pressure (~15 mm Hg) results in smaller relative deformations ventrally, given higher abdominal wall masses. In one aspect, the model disclosed here uses a quadratic curve for predicting distention factor as a function of BMI, as shown by the red curve in FIG. 6. The distention factor may thus be stored in a computer-readable medium as a variable which is a function of body mass index, BMI.

In one aspect, the parameters of the torso elliptic cylinder (such as the five shown in the example of FIG. 3 above) can be instantiated for a relatively small number of different sizes that are expected to sufficiently cover a large population of humans. Based on analysis of anthropometric measures of stature and bariatricity, the latter being represented by waist circumference, that were taken for a given population of males and females, four "patient reference sizes" were selected as seen in FIGS. 7A-7D. A patient reference size is a torso model that is selected to be representative of a statistically important group of actual torso sizes. Note that for finer granularity, more than four patient reference sizes may be determined. More generally, the model may be composed of two or more patient reference sizes.

Normalized Cylindrical Coordinates

An aspect of the parametric, geometric patient model is how it can be used to map a point such as a surgical target location inside the elliptical cylinder of a "nominal" torso model to an equivalent point in a parametric, geometric reference patient size (a torso model of arbitrary size.) This can be accomplished via normalized cylindrical coordinates which are defined below.

Figure 8:
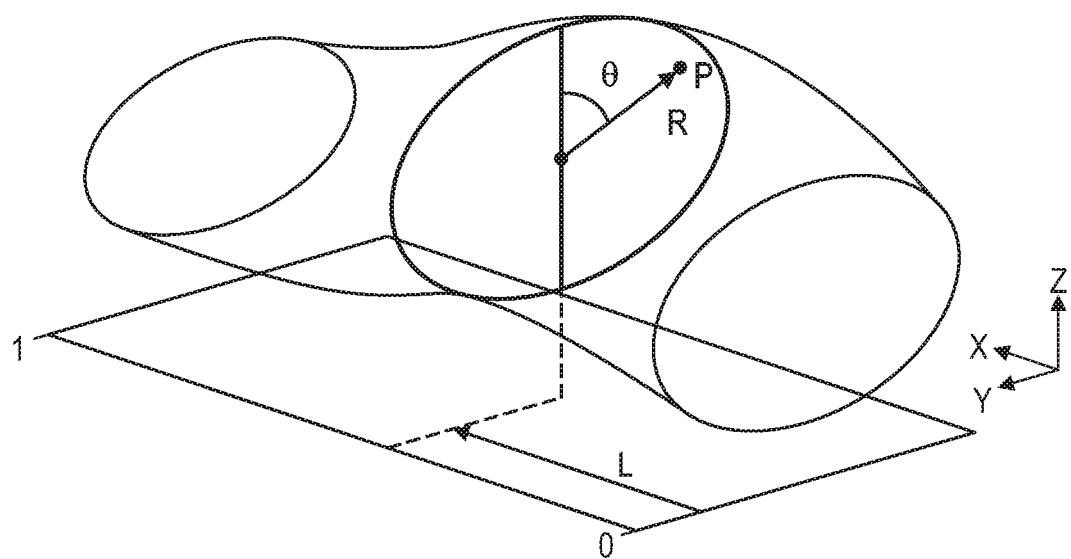
FIG. 8 illustrates an example of normalized coordinates on the elliptic cylinder.

Given a torso model surface S with the following characteristics: symmetric with respect to the midsagittal plane (XZ plane) and having cross-sections along transverse planes (parallel to the YZ plane) that are closed convex curves (like ellipse duos), then a point P can be located with respect to the center of a cross-section with coordinates {L, θ, R} as follows (and also see FIG. 8):

L: Normalized (dimensionless) distance along X axis (longitudinal direction of the torso model) and having a range $0 \le L \le 1$ and key values L=0 at hip plane, L=1 at upperchest plane (suprasternale level);

R: Normalized (dimensionless) distance from center of cross-section (lateral plane) to point P, where Normalization is with respect to distance to control surface along R having a range $R \ge 0$ and key values $0 \le R < 1$ inside control surface, R=1 at control surface, and R>1 outside control surface; and Theta (θ): Angle between +Z axis and R vector (in the cross-section, or lateral plane) where theta (θ) is positive if P is on patient's right side, negative if P is on patient's left side and has a range $-180° < theta (θ) \le 180°$ with key value theta (θ)=0 at midsagittal plane.

Normalized Surgical Targets

In one aspect of the disclosure here, a surgical target location (representative of a specific surgical procedure such as gastrectomy, gastric bypass, and cholecystectomy, to name a few) in the parametric, geometric patient model is given in normalized coordinates, where these are then mapped by the processor to the coordinates of the "corresponding" target location in the torso model of a particular size of patient. In other words, the same surgical target location given by a set of normalized cylindrical coordinates, for example as defined above, can be mapped to varying, corresponding and un-normalized target locations in patient models of different sizes. The normalized coordinates are expressed relative to a torso model reference frame (e.g., FIG. 1) and a torso model reference surface (e.g., FIG. 2.) This mapping process (normalized to un-normalized) relies on the patient surfaces defined by the model and discussed above, e.g., the insufflated state external surface and the insufflated state visceral surface. Referring to FIG. 1, the reference frame of the torso model may be defined as follows:

Origin, intersection of the hip plane, dorsal plane, and midsagittal plane;

X axis, along the caudocranial axis, positive in the cranial direction;

Z axis, along the dorsoventral axis, positive in the ventral direction; and

Y axis, along the lateral axis, positive toward the patient's right side, and where FIG. 4 depicts the visceral surface in non-insufflated state.

Figure 9:
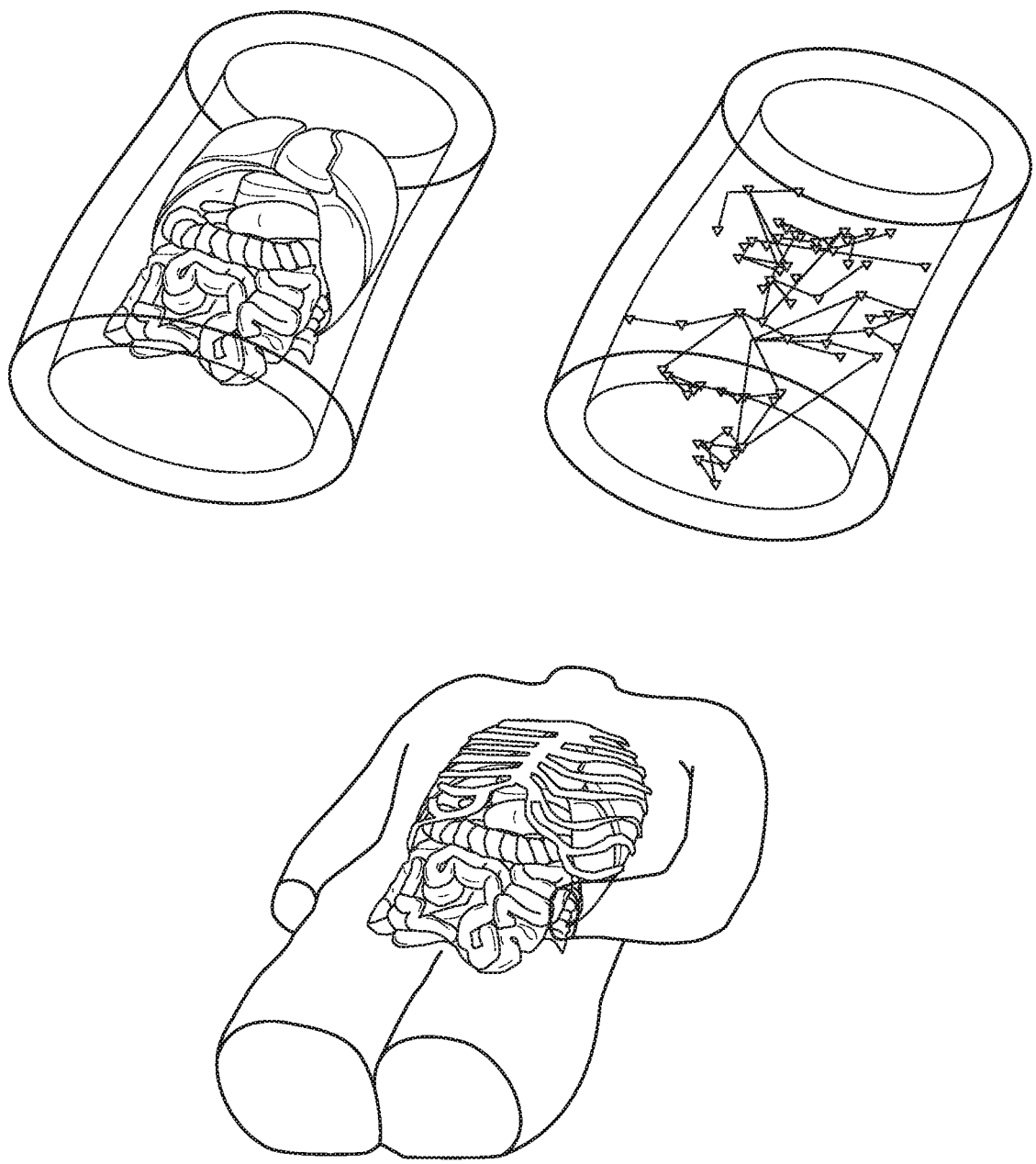
FIG. 9 visualizes a process for deriving surgical target locations from a reference specimen.
Figure 10A:
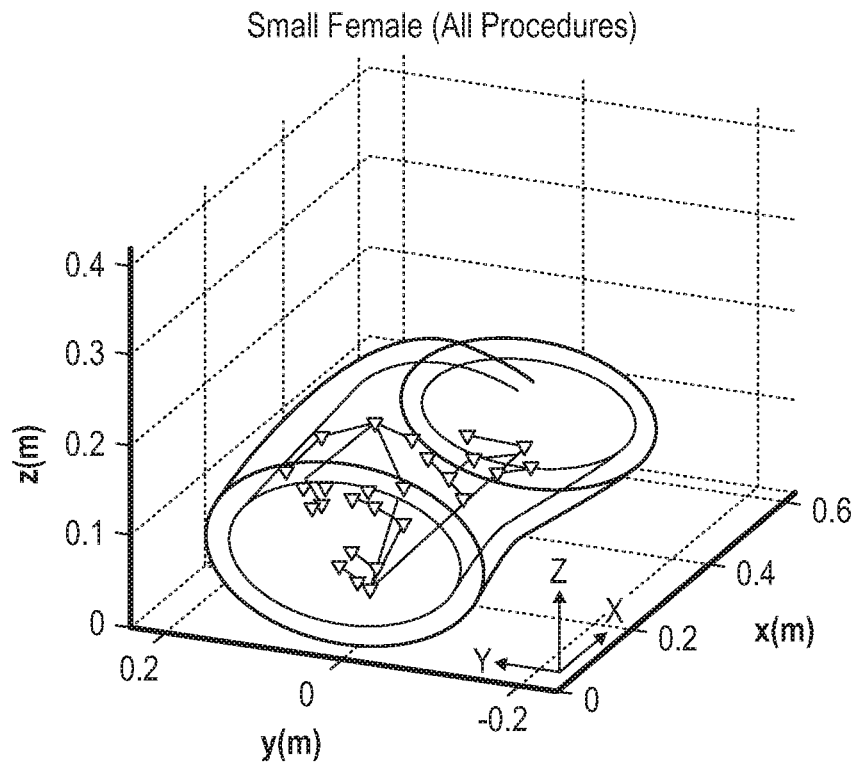
FIGS. 10A-10D illustrates surgical targets including activity paths in four example patient sizes.
Figure 10B:
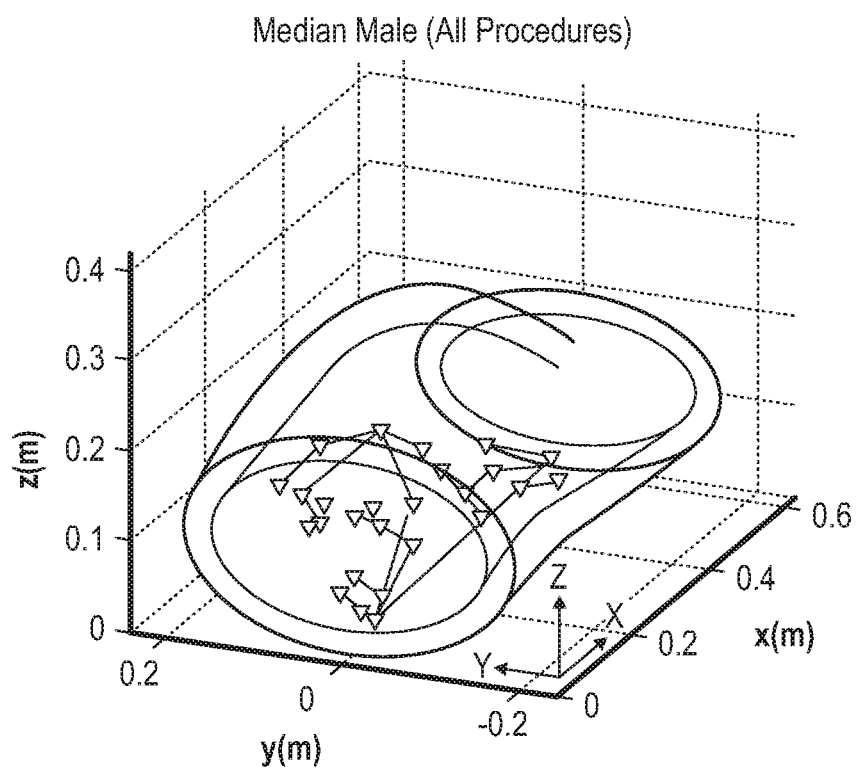
Figure 10C:
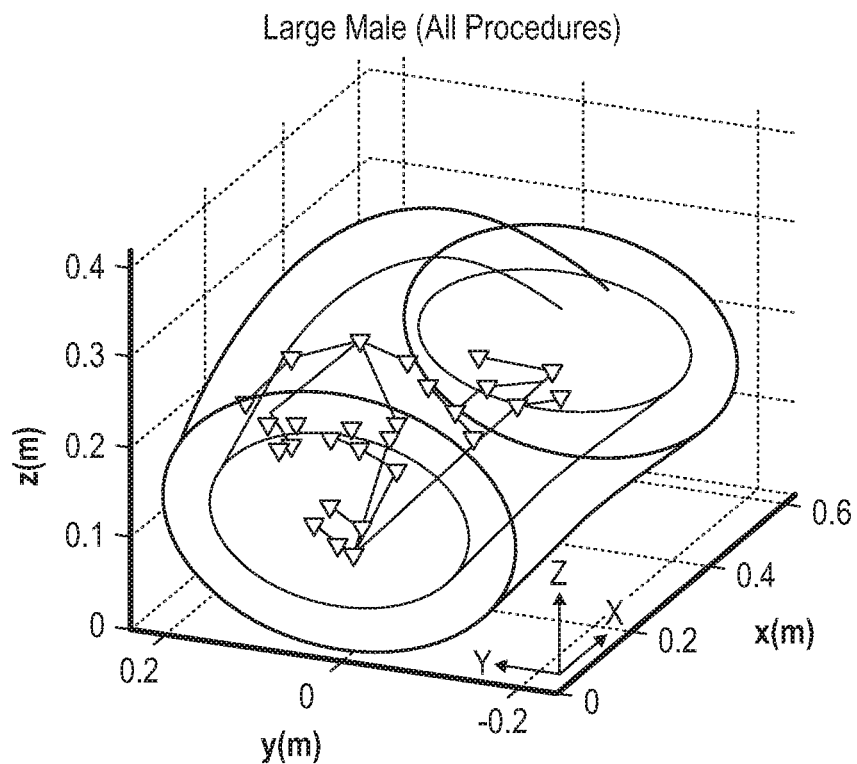
Figure 10D:
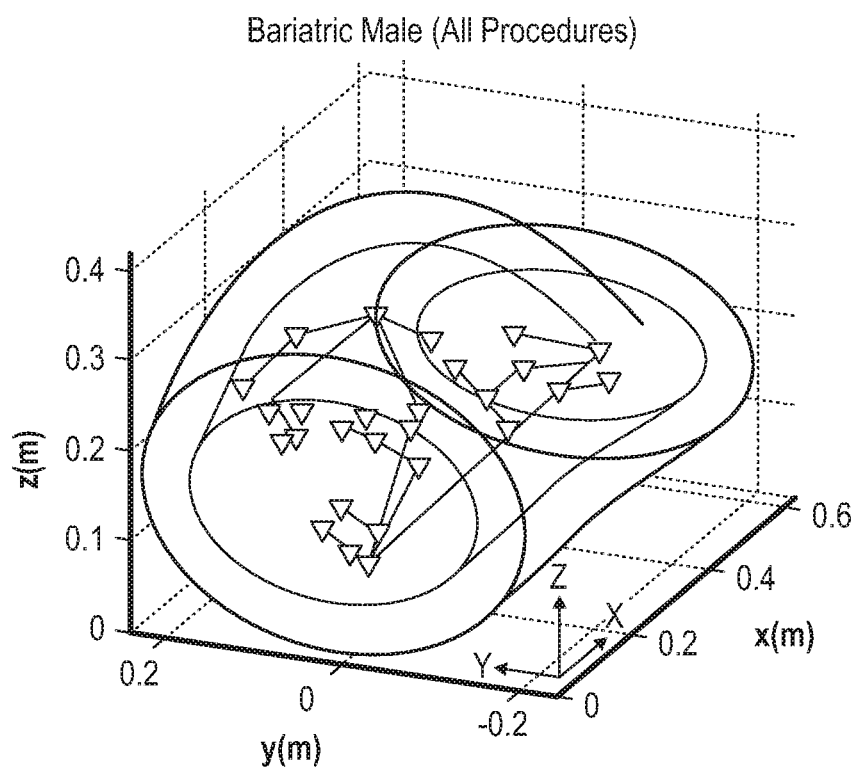

A surgical target location is normalized relative to an optimally-fitted visceral surface (discussed above). Also, a surgical target location does not necessarily correspond to an exact anatomical location in the model, as a surgeon may apply reasonable clinical judgment to determine a "generic" target location. FIG. 9 visualizes a process for deriving surgical target locations from a reference specimen, normalized relative to an optimally-fitted visceral surface from the same model. The table below gives an example data structure of several normalized surgical targets where each row specifies a target point expressed in normalized coordinates {L, Theta, R} describing a location of interest in a given surgical procedure:

| procedure | activity | target | L | Theta_deg | R | parietal | positioning | target verbose |
|---|---|---|---|---|---|---|---|---|
| GTM | GTM 1 | BodyDist | 0.43 | −28 | 0.81 | 0 | supine | Distal body of the stomach |
| GTM | GTM 1 | BodyProx | 0.66 | −80 | 0.61 | 0 | supine | Proximal body of the stomach |
| GTM | GTM 1 | LcurvSup | 0.64 | −123 | 0.22 | 0 | supine | Superior lesser curvature of the stomach |
| GTM | GTM 1 | Lcurvinf | 0.51 | −37 | 0.34 | 0 | supine | Inferior lesser curvature of the stomach |
| GTM | GTM 1 | HiatAnt | 0.7 | −121 | 0.2 | 0 | supine | Anterior Hiatus |

Using the methods described earlier, a given set of normalized surgical targets are then mapped to the four reference patient sizes—see FIG. 10 for an example of four patient sizes. Thus, for a particular type of minimally invasive surgical procedure and a given set of normalized target locations that need to be reached in such a surgery, the corresponding set of target locations in each of several (in this case, four) patient sizes are computed. The corresponding set of target locations (in a particular reference patient size) can then be used along with locations of the access ports on that particular reference patient size and a given surgical tool geometry, to determine in a pass/fail manner whether or not the given surgical tool geometry reaches the target surgical locations.

Port Placement

Once there is knowledge of where in a torso model a surgical tool needs to reach, as computed above using the normalized surgical target location, one or more access ports need to be described, or rather the location of a port in terms of normalized coordinates {L, θ, R} as defined above needs to be determined that will allow the surgical tool (when inserted into that port) to reach the normalized surgical target location. Note that here R is referring to a port location, and lies on an access surface, which may be the external surface, the visceral surface, or somewhere in between (within the abdominal wall.) The reach region and no-reach region on the access surface is referred to here as a reachability map.

It should also be noted that a given port location may be applicable to more than one of the several available patient reference sizes. See PPG, Table 5.1 for an example of reference ports.

The following criteria enable the determination of port locations that are consistent with geometric constraints, while accounting for specific surgical procedures (and their associated surgical target locations), different patient sizes, and of course constrained tool lengths. The criteria are related to reach capability and collision avoidance. Reference port locations (expressed in normalized coordinates as defined above) are described that can be used as a guide when choosing port locations for patients of varying sizes. The criteria rely on a torso model reference frame such as the one described above in connection with FIG. 1 and FIG. 2. A port surface may be defined as a surface on which the ports are located, and is constrained to be on the ventral half of the torso model (for procedures where the patient is placed supine.) A reachability map is constructed by evaluating (grid-wise) whether all of the one or more applicable surgical target locations, e.g., see the table above, can be reached from a given port location. In doing so, constraints are applied, namely maximum and minimum tool reach distances that are achievable by a tool (also referred to here as the tool reach range of a surgical tool.) The tool implementation may be assumed to be that of a straight shaft sliding on a frame, and the frame pivots relative to a fixed point (the port, e.g., at a remote center of motion, RCM, that is maintained by a surgical robotic system controller). The tool reach range may be specified for two types of tools: a surgical instrument (such as a needle driver or a grasper) and an endoscope.

The limits of the tool reach range may be defined as follows: For a surgical instrument, the upper limit for reach is the maximum distance between the port (at the remote center of motion, RCM) and the end of the tool shaft that corresponds to the proximal tool wrist), and the lower limit is the distal edge of a standard cannula (trocar.) For an endoscope, the upper limit for reach is the maximum distance between the port (at the RCM) and the distal edge of the working distance. The lower limit is the distal edge of a standard cannula plus the minimum working distance.

Figure 11:
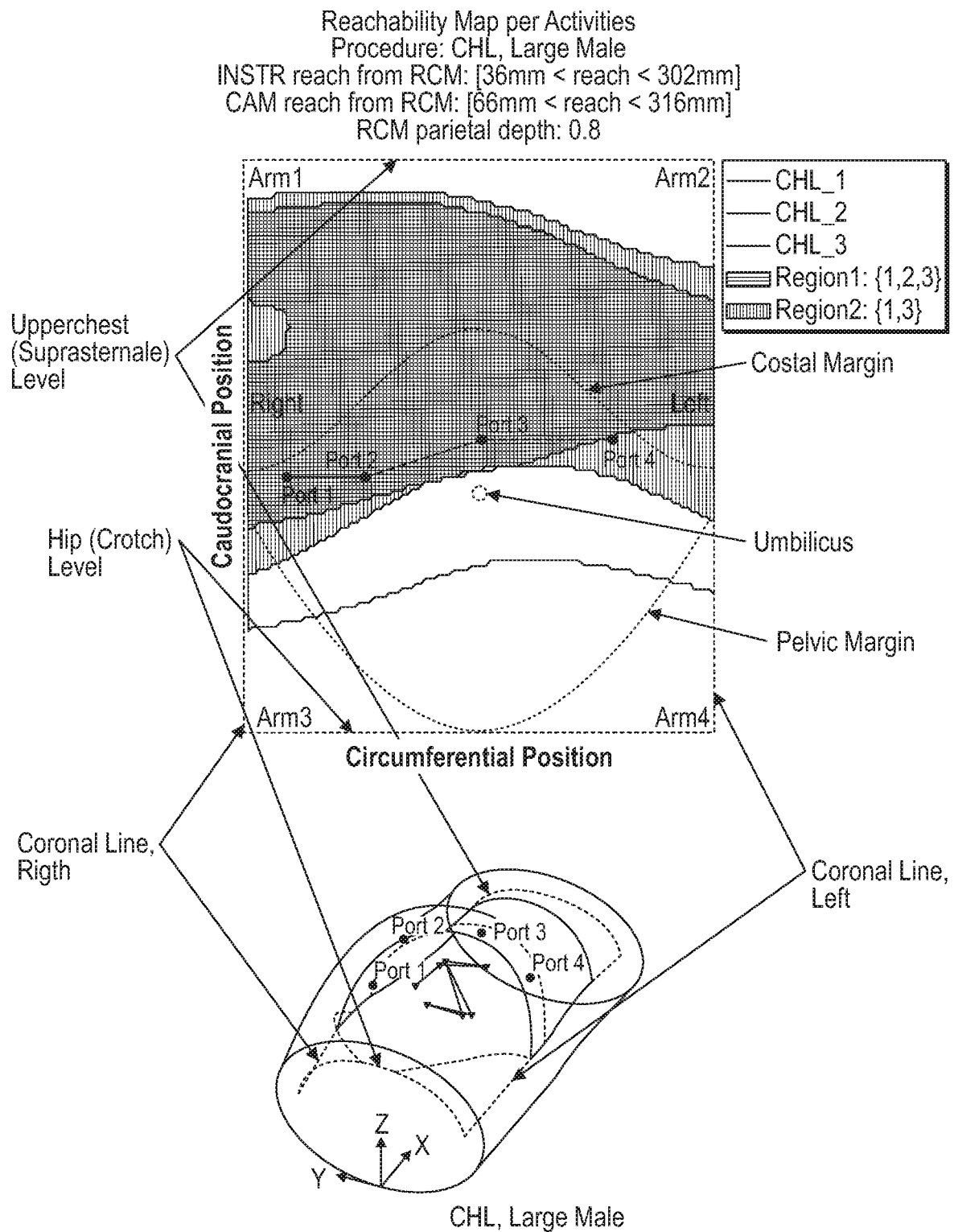
FIG. 11 shows an example reachability map in connection with the elliptic cylinder.

A reachability map is then computed for a selected tool and a selected surgical procedure (with the associated surgical target locations.) The reachability map contains a reach region and a no-reach region. If a port is placed in the reach region, then the selected tool (when inserted into that port) can reach the associated surgical target locations. In other words, the associated surgical target locations are within the specified tool reach range of that selected tool when the tool is inserted into a port that is placed win the reach region. If a port is placed in the no-reach region, then the selected tool (when inserted into that port) cannot reach the associated surgical target locations. The reachability map enables a more objective approach to port placement. For a port to be viable in terms of reach, it must be placed within the reach region that has been computed for the selected tool. Viable ports are shown within triangles in the example reachability map of FIG. 11.

A process for creating the reachability map can be described using the following example. Assume that a given surgical procedure has several activities or phases, and each activity may require the tool to reach a respective set of surgical target locations which are indicated in a parametric, geometric patient torso model. A candidate port location is selected. If the candidate port location does not allow the tip of the tool to reach all of the sets of surgical target locations (for all of the activities needed in the surgical procedure), then that candidate port location is categorized as part of the no-reach region. In other words, for a candidate port to be categorized into the reach region, the surgical target locations of all activities associated with the given surgical procedure need to be reachable from that port. The process repeats with different candidate port locations, categorizing each as being either in the reach region or in the no-reach region, not both. In some instances, there may be no single port location that allows the tool to reach the target locations for all activities of a given surgical procedure. In that case, there may need to be a port change during the surgical procedure in order for the tool to reach all target locations of all activities of that procedure (from at least two different port locations.)

Another criterion for port placement (or a further constraint for determining the reachability map) may be that the surgical tool tip needs to be able to traverse or move along each of a set of target paths. A target path connects two or more surgical target locations. Thus, the (port placement) reach region now also needs to allow the surgical tool (having a given tool reach range at its tip) to traverse all of the set of target paths that are required for the associated surgical procedure.

Yet another criterion for port placement may be to require a minimum distance between ports, to help avoid collisions between two or more tools (that have been inserted into those ports.) In order to allow for reasonable spacing of hardware around a port, a limit for minimum distance between ports is needed. To reduce the occurrence of collisions in the vicinity of ports a lower limit for minimum distance of 50 mm or more may be chosen. Additional guidance for port placement may be added to the reachability map process, as simplified representations of the costal margin, pelvic margin and umbilicus. These are dimensioned by specific anthropometric parameters for the chosen patient size (e.g., iliocristale height, tenth rib height, xiphoid process height and waist height).

As described above in detail and using examples, one aspect of the disclosure here is a computer system for providing guidance on the placement of surgical ports, the system comprising: a processor; and memory having stored therein the following data structures, a plurality of reference patient sizes each being a torso model of a different size and that defines an external surface and a visceral surface each having a dome shape that takes into account an insufflation effect, a set of normalized surgical target locations for a given surgical procedure, and a mapping of the set of normalized surgical target locations to a plurality of sets of corresponding or un-normalized surgical target locations, wherein each set of corresponding surgical target locations is in a respective one of the plurality of reference patient sizes, and a plurality of reachability maps each map showing a reach region and a no-reach region on a respective one of the plurality of reference patient sizes, wherein i) locating a surgical tool port in the reach region allows a surgical tool, that has been inserted through the surgical port, to reach all of the set of corresponding surgical target locations, and ii) locating the surgical tool port in the no-reach region does not allow the surgical tool to reach all of the set of corresponding surgical target locations. The normalized surgical target locations may be in normalized cylindrical coordinates L, theta, and R where L is distance in a longitudinal direction of the torso model, theta is angle in a lateral plane of the torso model, and R is distance in the lateral plane. The torso model may comprise a plurality of cross sections being elliptical, wherein one of the cross sections consists of two half ellipses, a ventral or upper half ellipse joined to a dorsal or bottom half ellipse, that have different radii of curvature. In particular, said one of the cross sections that consists of two half ellipses may be through a waist plane of the torso model. In addition, the torso model may be derived from a non-insufflated state torso model, by increasing ventral radius of the elliptical cross section that is through the waist plane while leaving unchanged other elliptical cross sections of the non-insufflated state torso model. Even more particularly, the ventral radius may be increased by a distention factor that is given by a quadratic curve as a function of body mass index, BMI.

In one aspect, the torso model defines an external surface and a visceral surface, and surgical tool ports are to be located on an access surface which is on the external surface, on the visceral surface, or in between the external surface and the visceral surface.

In one aspect, each of the plurality of reachability maps has been determined for the same surgical procedure and the same range of tool reach.

In yet another aspect of the computer system, the memory has stored therein a further data structure that includes a plurality of sets of target paths in the plurality of reference patient sizes, respectively, wherein each target path connects two or more surgical target locations, and wherein the reach region is determined so that locating the surgical tool port in the reach region allows the surgical tool to reach all of the set of target paths.

Also as described above, in detail and using examples, is a computer system for providing guidance on placement of surgical ports for minimally invasive surgery, the system comprising: a processor; and memory having stored therein data structures that include a plurality of reference patient sizes each being a torso model of a different size and that defines an external surface and a visceral surface, a plurality of sets of surgical target locations, wherein each set of surgical target locations is inside a volume of a respective one of the plurality of reference patient sizes, and a plurality of sets of permissible port locations wherein each set of permissible port locations is on one of the plurality of reference patient sizes, wherein each permissible port location, of a set of permissible port locations, has been selected such that a surgical tool having specified reach characteristics and placed at the permissible port location, can reach all of the set of surgical target locations inside the reference patient size. In particular, the torso model may be dome shaped due to insufflation effects that have been intentionally taken into account.

Also as described above, in detail and using examples, is a method for determining surgical port placement for minimally invasive surgery, the method comprising: receiving a plurality of measurements of a patient including two or more of the group consisting of stature, waist circumference, body mass index (BMI), and gender; selecting one of a plurality of reference patient sizes based on the plurality of measurements, wherein each of the reference patient sizes is a torso model of a different size and that defines an external surface and a visceral surface; receiving an identification of a surgical procedure; receiving an identification of or characteristics of a surgical tool; and performing a table lookup based on the selected reference patient size, the identification of a surgical procedure, and the identification of or characteristics of a surgical tool, wherein the table lookup directly produces a set of permissible port locations on the selected reference patient size. The permissible port locations may have been previously determined and stored in a lookup table. The plurality of measurements may comprise stature and waist circumference. The set of permissible port locations may be given in normalized cylindrical coordinates, and in that case the method may further comprise mapping the set of permissible port locations from normalized cylindrical coordinates to un-normalized coordinates on the selected reference patient size.

In one aspect, the method further comprises accessing a lookup table that is associated with the selected reference patient size, wherein the lookup table associates the identification of a surgical procedure to a set of surgical target locations inside the selected reference patient size.

Also as described above in detail and using examples, is a method for determining whether or not a surgical tool model can reach the surgical target locations of a minimally invasive surgery, the method comprising: receiving characteristics of a surgical tool; and performing a table lookup based on the characteristics of a surgical tool, to determine whether or not there is a matching entry in a plurality of entries of a lookup table that contains matching surgical tool characteristics, wherein each of the plurality of entries of the lookup table contains i) a reference patient size, ii) an identification of a surgical procedure, iii) a set of permissible port locations on the selected reference patient size, and iv) surgical tool characteristics. The characteristics of the surgical tool may comprise a tool reach range. If the surgical tool is a surgical instrument, then the tool reach range comprises: an upper limit being the maximum distance between a permissible port location and the end of a tool shaft that corresponds to a proximal tool wrist; and a lower limit being a distal edge of a cannula. If the surgical tool is an endoscope, then the tool reach range comprises: an upper limit being the maximum distance between a permissible port location and a distal edge of a working distance of the endoscope; and a lower limit being i) a distal edge of a cannula plus ii) a minimum working distance of the endoscope.

In one aspect of the method, in the set of permissible port locations, a distance between i) a permissible port location and ii) each surgical target location of a set of surgical target locations associated with a given surgical activity that is associated with the identification of a surgical procedure, falls within the tool reach range of the surgical tool.

Another application of the concepts described above is a validation process which is used to prove that a given design for a surgical robotic arm and its attached surgical tool reaches a surgical target location in a selected one of the reference patient sizes and avoids collisions, wherein a collision may be between two or more arms or between an arm and the patients skin. The collisions are avoided while the tips of the tools traverse given paths between various surgical target locations.

Another aspect of the disclosure here is a computer-implemented method (a method performed by one or more digital processors that have been configured according to instructions stored in memory of a computer system) for determining surgical port placement for minimally invasive surgery. The method is as follows. A plurality of measurements of a patient are received, e.g., comprising one or more measurements obtained from a medical imaging procedure or from a manual measurement, performed on the patient. Based on the received measurements, an instance of a parametric torso model is determined that defines an external surface and a visceral surface each having a dome shape that takes into account an insufflation effect. An identification of a surgical procedure is received, and in response a set of normalized surgical target locations in the parametric torso model are determined. This set of normalized surgical target locations is then mapped to a set of un-normalized surgical target locations in the instance of the parametric torso model. The characteristics of a surgical tool are also received. A set of permissible port locations on the instance of the parametric torso model are computed, based on the characteristics of the surgical tool and based on the set of un-normalized surgical target locations. This set of permissible port locations may then be presented to a surgeon during surgery on the patient, based on which the surgeon can decide where on the patient's abdomen to place the port.

As explained above, the parametric torso model may comprise an elliptical cylinder having at least four elliptical cross sections at hip plane, waist plane, chest plane and upper chest plane. The waist plane elliptical cross section may consist of two half ellipses that have different radii of curvature, namely a ventral or upper half ellipse joined to a dorsal or bottom half ellipse.

When determining an instance of a parametric torso model, the external surface for an insufflated state may be derived by applying a distention factor to a non-insufflated state external surface. The distention factor may vary as a function of body mass index, BMI. In other cases, when determining an instance of a parametric torso model, the external surface is directly generated based on the received plurality of measurements which been taken while the patient was insufflated.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. The description is thus to be regarded as illustrative instead of limiting.

What is claimed is:

1. A method for determining a set of permissible surgical port locations for a given minimally invasive surgery, MIS, surgical tool, the method comprising:
   receiving a plurality of measurements of a patient;
   determining, based on the received measurements, an instance of a parametric torso model having a dome shape that takes into account an insufflation effect;
   receiving an identification of a surgical procedure and in response determining a set of normalized surgical target locations in the parametric torso model;
   mapping the set of normalized surgical target locations to a set of un-normalized surgical target locations in said instance of the parametric torso model;
   receiving characteristics of a surgical tool, wherein the surgical tool is to be coupled to a robotic arm or is a hand-held surgical instrument;
   computing a set of permissible port locations on said instance of the parametric torso model, based on the characteristics of the surgical tool and based on the set of un-normalized surgical target locations; and
   producing a reachability map based on the computed set of permissible port locations, wherein the reachability map indicates a reach region and a no-reach region on an access surface of said instance of the parametric torso model.

2. The method of claim 1 wherein the plurality of measurements of the patient comprises one or more measurements obtained from a medical imaging procedure performed on the patient.

3. The method of claim 1 wherein the parametric torso model comprises an elliptical cylinder having at least four elliptical cross sections at hip plane, waist plane, chest plane and upper chest plane.

4. The method of claim 3 wherein the waist plane elliptical cross section consists of two half ellipses that have different radii of curvature.

5. The method of claim 4 wherein the two half ellipses are a ventral or upper half ellipse joined to a dorsal or bottom half ellipse.

6. The method of claim 1 wherein determining an instance of a parametric torso model comprises
   deriving an external surface for an insufflated state by applying a distention factor to a non-insufflated state external surface.

7. The method of claim 6 wherein the distention factor varies as a function of body mass index, BMI.

8. The method of claim 1 wherein determining an instance of a parametric torso model comprises
directly generating an external surface based on the received plurality of measurements having been taken while the patient was insufflated.

9. A computer system for determining surgical port placement for minimally invasive surgery, the computer system comprising:
a processor; and
memory having stored therein instructions that configure the processor to
receive a plurality of measurements of a patient,
determine, based on the received measurements, an instance of a parametric torso model that defines an external surface and a visceral surface each having a dome shape that takes into account an insufflation effect,
receive an identification of a surgical procedure and in response determining a set of normalized surgical target locations in the parametric torso model,
map the set of normalized surgical target locations to a set of un-normalized surgical target locations in the instance of the parametric torso model,
receive characteristics of a surgical tool wherein the surgical tool is to be coupled to a robotic arm or is a hand-held surgical instrument,
compute a set of permissible port locations on said instance of the parametric torso model, based on the characteristics of the surgical tool and based on the set of un-normalized surgical target locations, and
produce a reachability map based on the computed set of permissible port locations, wherein the reachability map indicates a reach region and a no-reach region on an access surface of said instance of the parametric torso model.

10. The computer system of claim 9 wherein the plurality of measurements of the patient comprises one or more measurements obtained from a medical imaging procedure performed on the patient.

11. The computer system of claim 9 wherein the parametric torso model comprises an elliptical cylinder having at least four elliptical cross sections at hip plane, waist plane, chest plane and upper chest plane.

12. The computer system of claim 11 wherein the waist plane elliptical cross section consists of two half ellipses that have different radii of curvature.

13. The computer system of claim 12 wherein the two half ellipses are a ventral or upper half ellipse joined to a dorsal or bottom half ellipse.

14. The computer system of claim 9 wherein the processor determines an instance of a parametric torso model by
deriving the external surface for an insufflated state by applying a distention factor to a non-insufflated state external surface.

15. The computer system of claim 14 wherein the distention factor varies as a function of body mass index, BMI.

16. The computer system of claim 9 wherein the processor determines an instance of a parametric torso model by
directly generating the external surface based on the received plurality of measurements having been taken while the patient was insufflated.

17. An article of manufacture comprising a computer-readable storage medium having stored therein instructions that configure a processor to determine a set of permissible surgical port locations for minimally invasive surgery, by configuring the processor to
receive a plurality of measurements of a patient,
determine, based on the received measurements, an instance of a parametric torso model that defines an external surface and a visceral surface each having a dome shape that takes into account an insufflation effect,
receive an identification of a surgical procedure and in response determining a set of normalized surgical target locations in the parametric torso model,
map the set of normalized surgical target locations to a set of un-normalized surgical target locations in the instance of the parametric torso model,
receive characteristics of a surgical tool, wherein the surgical tool is to be coupled to a robotic arm or is a hand-held surgical instrument,
compute a set of permissible port locations on said instance of the parametric torso model, based on the characteristics of the surgical tool and based on the set of un-normalized surgical target locations, and
produce a reachability map based on the computed set of permissible port locations, wherein the reachability map indicates a reach region and a no-reach region on an access surface of said instance of the parametric torso model.

18. The article of manufacture of claim 17 wherein the plurality of measurements of the patient comprises one or more measurements obtained from a medical imaging procedure performed on the patient.

19. The article of manufacture of claim 17 wherein the processor determines an instance of a parametric torso model by
deriving the external surface for an insufflated state by applying a distention factor to a non-insufflated state external surface.

20. The article of manufacture of claim 19 wherein the computer-readable storage medium has stored therein the distention factor as a variable which is a function of body mass index, BMI.

\* \* \* \* \*